(12) United States Patent
Beaudoin

(10) Patent No.: US 12,350,346 B2
(45) Date of Patent: Jul. 8, 2025

(54) CONJUGATES ENHANCING TOTAL CELLULAR ACCUMULATION

(71) Applicant: DEFENCE THERAPEUTICS INC., Vancouver (CA)

(72) Inventor: Simon Beaudoin, Sherbrooke (CA)

(73) Assignee: DEFENCE THERAPEUTICS INC., Sherbrooke (CA)

( * ) Notice: Subject to any disclaimer, the term of this patent is extended or adjusted under 35 U.S.C. 154(b) by 0 days.

(21) Appl. No.: 18/351,291

(22) Filed: Jul. 12, 2023

(65) Prior Publication Data
US 2024/0016960 A1    Jan. 18, 2024

Related U.S. Application Data

(63) Continuation of application No. PCT/CA2022/051527, filed on Oct. 17, 2022.

(60) Provisional application No. 63/256,726, filed on Oct. 18, 2021.

(51) Int. Cl.
| | |
|---|---|
| *A61K 51/10* | (2006.01) |
| *A61K 45/00* | (2006.01) |
| *A61K 47/54* | (2017.01) |
| *A61K 47/64* | (2017.01) |
| *A61K 47/68* | (2017.01) |
| *C07K 16/30* | (2006.01) |

(52) U.S. Cl.
CPC .......... *A61K 47/6817* (2017.08); *A61K 45/00* (2013.01); *A61K 47/554* (2017.08); *A61K 47/645* (2017.08); *A61K 47/6851* (2017.08); *A61K 51/1045* (2013.01); *C07K 16/3015* (2013.01); *C07K 2319/09* (2013.01)

(58) Field of Classification Search
CPC .......................... A61K 47/6851; A61K 47/554
See application file for complete search history.

(56) References Cited

U.S. PATENT DOCUMENTS

| | | | |
|---|---|---|---|
| 5,446,026 A * | 8/1995 | Ruff .................... | C07K 14/585 |
| | | | 530/328 |
| 5,955,365 A | 9/1999 | Szoka et al. | |
| 7,732,177 B2 | 6/2010 | Iadonato et al. | |
| 11,291,717 B1 | 4/2022 | Beaudoin | |
| 11,352,437 B2 | 6/2022 | Beaudoin et al. | |
| 2022/0218820 A1 | 7/2022 | Beaudoin | |

FOREIGN PATENT DOCUMENTS

| | | |
|---|---|---|
| CN | 100588425 | 2/2010 |
| EP | 1 046 394 A2 | 10/2000 |
| WO | WO-2017/156630 | 9/2017 |
| WO | WO-2018/165752 | 9/2018 |
| WO | WO-2020/252298 A1 | 12/2020 |
| WO | WO-2022/126239 A1 | 6/2022 |
| WO | WO-2022/232945 A1 | 11/2022 |

OTHER PUBLICATIONS

U.S. Appl. No. 18/046,718, filed Oct. 14, 2022.
Al-Hilal et al., "Functional transformations of bile acid transporters induced by high-affinity macromolecules," Scientific Reports 4:4163, 9 pages (2014).
Anding et al., (2017). Cleaning House: Selective Autophagy of Organelles. Devopmental Cell, 41(1):10-22.
Anguille et al., (2014). Clinical use of dendritic cells for cancer therapy. Lancet Oncology, 15(7): e257-67.
Azuar et al., (2019). Cholic Acid-based Delivery System for Vaccine Candidates against Group A *Streptococcus*. ACS Medicinal Chemistry Letters, 10: 1253-1529.
Beaudoin et al., (2016). Antibodies with integrated endosome escape and multi directional intracellular trafficking control capabilities for molecular transport and accumulation of a BODIPY based dye. J Nucl Med, vol. 57 No. supplement 2 1215.
Beaudoin et al., (2016). ChAcNLS, a novel modification to antibody-conjugates permitting target cell-specific endosomal escape, localization to the nucleus and enhanced total intracellular accumulation. Molecular Pharmaceutics, 13(6): 1915-26.
Beaudoin et al., (2018). Initial Evaluation of Antibody-conjugates Modified with Viral-derived Peptides for Increasing Cellular Accumulation and Improving Tumor Targeting. Journal of Visualized Experiments, 133: 55440. doi: 10.3791/55440.
Beck et al., (2017). Strategies and challenges for the next generation of antibody-drug conjugates. Nature Reviews Drug Discovery, 16: 315-337.
Chang et al. (2004) Bile acids are essential for porcine enteric calicivirus replication in association with down-regulation of signal transducer and activator of transcription 1", PNAS, vol. 101, No. 23.
Chugh et al. (2010) Cell-Penetrating Peptides : Nanocarrier for Macro molecule Delivery in Living Cells, IUBMB Life, 62 (3): 183-193.
De Loos, M. et al.1 (2005). Design and Application of Self-Assembled Low Molecular Weight Hydrogels. Eur. J. Org. Chem., 3615-3631.
El-Kadiry et al., (2022), Accum Technology: A Novel Conjugable Primer for Onco-Immunotherapy. Molecules, 27(12): 3807, doi: 10.3390/molecules27123807.
Hanafi et al., (2018). Overview of Bile Acids Signaling and Perspective on the Signal of Ursodeoxycholic Acid, the Most Hydrophilic Bile Acid, in the Heart. Biomolecules, 8(4): 159.

(Continued)

*Primary Examiner* — James W Rogers
(74) *Attorney, Agent, or Firm* — Michael L. Jespersen; Foley & Lardner LLP

(57) ABSTRACT

The present description relates to a conjugated compound an antibody covalently linked to enhancer moiety composed by a nuclear localization sequence (NLS), covalently linked to a sterol variant, such as cholic acid (ChAc) or a variant thereof. The enhancer moiety as encompassed herein is able to induce endosome escape of the compound-conjugates by direct membrane destabilization or indirectly by ROS and ceramide production which destabilize endosome-lysosome membrane. The conjugated compound can further comprise payload.

14 Claims, 3 Drawing Sheets
Specification includes a Sequence Listing.

(56) References Cited

OTHER PUBLICATIONS

Kenney and Meng (2015). Identification and Fine Mapping of Nuclear and Nucleolar Localization Signals within the Human Ribosomal Protein S17, PLoS One Apr. 8, 2015;10(4):e0124396.
Kim et al. (2012) "Homodimeric SV40 Nls peptide formed by disulfide bond as enhancer for gene delivery", Bioorganic & Medicinal chemistry letters, vol. 22, pp. 5415-5418.
Kim et al. (2017) "The molecular mechanism for nuclear transport and its application", Anat Cell Biol; 50: 77-85.
Kosugi et al. (2009) "Six Classes of Nuclear Localization Signals Specific to Different Binding Grooves of Importin", J. Biol. Chem. 2009, 284 : 478-485.
Lacasse, V. et al., (2020). A Novel Proteomic Method Reveals NLS Tagging of T-DM1 Contravenes Classical Nuclear Transport in a Model of HER2-Positive Breast Cancer. Molecular Therapy: Methods & Clinical Development vol. 19, 99-119.
Lam and Dean, (2010) "Progress and prospects: nuclear import of nonviral vectors", Gene Therapy, 2010, 17, 439-447.
Leyton et al. (2011) "Auger Electron Radioimmunotherapeutic Agent Specific for the CD123 /CD131—Phenotype of the Leukemia Stem Cell Population." The Journal of Nuclear Medicine, vol. 52, No. 9, 1465-1473.
Linke, T. et al. (2001). Stimulation of Acid Sphingomyelinase Activity by Lysosomal Lipids and Sphingolipid Activator Proteins. Biol. Chem., vol. 382, pp. 283-290.
Liu et al., (2020), The Renpenning syndrome-associated protein PQBP1 facilitates the nuclear import of splicing factor TXNL4A through the karyopherin 2 receptor. Journal of Biological Chemistry, 295(13): 4093-4100.
Lu, J. et al., (2021). Types of nuclear localization signals and mechanisms of protein import into the nucleus. Cell Commun Signal 19:60.
Manoharan et al. (1994) "Cholic Acid—Oligonucleotide Conjugates for Antisense Applications", Bioorganic and Medicinal Chemistry Letter, vol. 4, No. 8, 1053-1060.
Murakami et al., (2020). Bile acids and ceramide overcome the entry restriction for GII.3 human norovirus replication in human intestinal enteroids. Proceedings of the National Academy of Sciences USA. 117(3):1700-1710.
Ogris et al., (2001). Melittin enables efficient vesicular escape and enhanced nuclear access of nonviral gene delivery vectors. Journal of Biological Chemistry, 276(50): 47550-5.
Paquette et al., (2016). ChAcNLSA14, a novel antibody conjugate PET tracer for targeting human IL 5Ra-positive muscle invasive bladder cancer. J Nucl Med, vol. 57 No. supplement 2 52.
Paquette et al., (2018). NLS-Cholic Acid Conjugation to IL-512a-Specific Antibody Improves Cellular Accumulation and In Vivo Tumor-Targeting Properties in a Bladder Cancer Model. Bioconjugate Chemistry. 29: 1352-1363.

Patel et al., (2017). Next generation approaches for tumor vaccination. Chinese Clinical Oncology. 6(2):19.
Raouane et al. (2012) "Lipid Conjugated Oligonucleotides : A Useful Strategy for Delivery", Bioconjugate Chemistry, vol. 23, pp. 1091-1104.
Ray et al. (2015) "Quantitative tracking of protein trafficking to the nucleus using cytosolic protein delivery by nanoparticle-stabilized nanocapsules" Bioconjug Chem. Jun. 17, 2015; 26 (6): 1004-1007. doi :10.1021/acs.bioconjchem.5b00141.
Sangeetha, N. M. et al., (2004). Properties of Hydrogels Derived from Cationic Analogues of Bile Acid: Remarkably Distinct Flowing Characteristics. J. Phys. Chem. B, 108, 16056-16063.
Shivanna et al., (2014) The crucial role of bile acids in the entry of porcine enteric calicivirus. Virology 456-457, 268-278.
Shivanna et al., (2015). Ceramide formation mediated by acid sphingomyelinase facilitates endosomal escape of caliciviruses. Virology, 483, 218-228.
Sun et al., (2016). Factors influencing the nuclear targeting ability of nuclear localization signals. Journal of Drug Targeting, 24(10): 927-933.
Swaan et al., (1997). Enhanced Transepithelial Transport of Peptides by Conjugation to Cholic Acid. 8: 520-525.
Tagliamonte et al., (2014). Antigen-specific vaccines for cancer treatment. Human Vaccines & Immunotherapeutics, 10(11): 3332-3346.
Tomatsidou (2013) "Evaluation of peptide-mediated nucleic acid delivery", Department of Pharmaceutics, Utrecht Institute of Pharmaceutical Sciences (UIPS), Utrecht University, 2013, pp. 1-33.
Wang et al., (2020). HMGB1 in inflammation and cancer. Journal of Hematology & Oncology, 13:116.
Pavlovic et al., "Bile Acids and Their Derivatives as Potential Modifiers of Drug Release and Pharmacokinetic Profiles," Frontiers in Pharmacology, Nov. 8, 2018.
Raucher, D. et al. (2015) "Cell-penetrating peptides: strategies for anticancer treatment", Trends Mol Med. Sep. 2015;21(9):560-70.
Final Office Action issued in U.S. Appl. No. 16/085,141 dated Jul. 17, 2020 (17 pages).
Martinez et al., "Different Bile Acids Exhibit Distinct Biological Effects: The Tumor Promoter Deoxycholic Acid Induces Apoptosis and the Chemopreventive Agent Ursodeoxycholic Acid Inhibits Cell Proliferation", Nutrition and Cancer, vol. 31, No. 2, May 7, 1998, pp. 111-118.
Non-Final Office Action issued in U.S. Appl. No. 16/085,141 dated Mar. 2, 2020 (15 pages).
Non-Final Office Action issued in U.S. Appl. No. 16/085,141 dated Nov. 18, 2020 (22 pages).
Day et al., "Stress-induced nuclear accumulation is dispensable for Hog1-dependent gene expression and virulence in a fungal pathogen", Scientific Reports, vol. 7, Oct. 30, 2017, pp. 1-11.
Shastry et al., "Rise of Antibody-Drug Conjugates: The Present and Future", Developmental Therapeutics, vol. 43, May 25, 2023, pp. 1-15.

* cited by examiner

|: Convalent link

Enhancer (MD----NLS): Membrane permeabilization Domain- cholic acid---NLS

NLS: Nuclear Localization signal

CONJUGATES ENHANCING TOTAL CELLULAR ACCUMULATION

CROSS-REFERENCE TO RELATED APPLICATION

The present application is the U.S. National Stage of PCT/CA2022/051527, filed Oct. 17, 2022, which claims priority which claims priority from U.S. Provisional Application No. 63/256,726 filed Oct. 18, 2021, the contents of which are hereby incorporated by reference in their entirety.

The instant application contains a Sequence Listing which has been submitted in XML format via Patent Center and is hereby incorporated by reference in its entirety. Said XML copy, created on Jul. 3, 2023, is named 136307-0303_sequence.xml and is 18,436 bytes.

TECHNICAL FIELD

The present relates to a conjugate compound that enhances total intracellular accumulation.

BACKGROUND ART

The design of antibody-conjugates (ACs) for delivering molecules for therapy or imaging applications in humans has sufficiently progressed to demonstrate clinical efficacy in certain malignancies and reduce systemic toxicity that occurs with standard chemotherapy or radiation.

ACs have demonstrated success to deliver payloads of drugs selectively against cancer cells for therapeutic or imaging applications in humans. However, AC technology, whether in the form of antibodies armed with radioactive isotopes or cytotoxic drugs, is still looking to develop into more effective and widely applicable pharmaceuticals for improved and more widespread cancer management.

The universal cornerstone for intracellular drug accumulation by antibody-drug conjugates (ADCs) is reliant on its cellular internalization pathway. Once bound to target antigen, ADCs are internalized and entrapped inside endosomes and trafficked to the lysosome. Lysosomes are membrane-enclosed organelles that contain an array of digestive enzymes and receive proteins transported by endosomes through vesicle membrane fusion and results in the release of active drug catabolites. The intracellular accumulation of these catabolites is directly correlated with cytotoxic potency. This dependency is what currently plagues ADCs and prevents them from achieving their full potential. Cancer cells respond to ADCs by increasing the expression of drug efflux pumps and decreasing the expression of target receptors. Receptor recycling pathways and their increased used by cancer cells has also been implicated to reduce the intracellular accumulation of the internalized ADCs. In essence, the field has long relied on an inefficient process for intracellular accumulation and there is no research directly addressing this problem. Therefore, avoiding entrapment in these intracellular pathways is an important area to improve the cellular accumulation of transported drugs and for maximizing ADC activity.

The functionalization of monoclonal antibodies (mAbs) with cell-penetrating peptides has resulted in remarkable increases in intracellular accumulation when cells are treated with these types of ACs. However, this advancement in AC cellular accumulation has been mostly for allowing mAbs to access and target specific molecules inside cells that would otherwise be unavailable for antibodies to target. Of the few reports that attempt to utilize ACs equipped with cell-penetrating peptides as therapeutic agents against cell surface cancer-specific receptors, all suffered from high accumulation in non-target cells or tissues and thus are limited in their application for targeted delivery.

Recent advancements whereby ACs functionalized with pH-sensitive polymers have shown impressive abilities to escape endosomes and enter the cytoplasm while maintaining target cell selectivity. However, it is yet to be determined whether increased escape by these ACs corresponds to an increase in intracellular accumulation.

Another recent advancement has been to empower ACs to achieve multi-selective targeting by attaching peptides that harbor compartment-localizing amino acids. In particular, the nuclear localization signal (NLS) sequence from SV-40 Large T-antigen has previously been incorporated into synthetic peptides and conjugated to proteins and demonstrated the ability to direct the transport of proteins into the nucleus. Although, the optimized NLS sequence is 25 amino acids long, the mAb 7G3 was conjugated to a 13-mer peptide (CGYG<u>PKKKRKV</u>GG) harboring a segment of the NLS (underlined) sufficient for nuclear translocation. An advantage of this short sequence is that it does not penetrate cells and allows mAbs to maintain cell selectivity. 7G3-NLS was used to deliver the radioisotope cargo indium-111 ($^{111}$In) inside the nucleus. Molecular damage by $^{111}$In is due to its emissions of energetic Auger electrons. Because they travel only nanometer-micrometer distances they are more effective if delivered inside the nucleus. Unfortunately, cytotoxicity was not overwhelming relative to standard $^{111}$In-7G3 and the evidence suggested was due to ineffective nuclear localization caused by entrapment in the endosomal-lysosomal and/or recycling pathways.

Recently, Leyton J V and Beaudoin S (WO 2017/156630) have shown that addition of ChAc molecule on the amine of the N-terminal Cysteine of the SV40 large T antigen NLS (SEQ ID NO: 1) by chemical reaction allow the peptide to acquire a new intracellular and nuclear enhancer delivery function by inducing it's escape from endosome-lysosome entrapment and its nuclear localization and accumulation. However, they also observed that addition of ChAc-SV40 large T antigen to an antibody induce a modification in the solubility, stability, biodistribution and pharmacokinetic of the antibodies. The only combination demonstrated therein is of SV40 large T antigen (as depicted in SEQ ID NO: 1) cholic acid. It is well known that each different bile acids have different activities. The best example showing this differential activity is some of the bile acids are classified as pro-inflammatory factor while other are known to have anti-inflammatory activity.

Therefore, there is still a need to be provided with AC intracellular enhancer delivery agents that is effective in circumventing the entrapment of the endosomal-lysosomal and/or recycling pathways.

SUMMARY

In accordance with the present description, there is now provided a conjugated compound comprising an antibody covalently linked to a nuclear localization sequence (NLS), said NLS covalently linked to sterol-variant, and wherein said antibody is not linked to a SV40 large T antigen NLS linked to cholic acid (ChAc). In an embodiment, wherein the sterol variant is cholic acid (ChAc) or a variant thereof.

In another embodiment, the NLS is SV40 large T antigen NLS combined with a sterol variant other than ChAc.

In an embodiment, the sterol variant can be positioned as provided herein on the C-terminal or N-terminal portion of the conjugated compound.

In another embodiment, the NLS is a NLS other than the SV40 NLS.

In a further embodiment, the NLS is a monopartite or bipartite NLS.

In another embodiment, the NLS is a non-classical NLS.

In an embodiment, wherein the non-classical NLS is a hydrophobic PY-NLS or a basic PY-NLS.

In an embodiment, the antibody is a monoclonal or polyclonal antibody.

In an embodiment, the antibody is a monospecific, bispecific or multispecific antibody.

In a further embodiment, the antibody is a mouse antibody, a goat antibody, a human antibody or a rabbit antibody.

In an embodiment, the antibody is a humanized antibody.

In another embodiment, the antibody comprises an epitope binding fragment selected from the group consisting of: Fv, F(ab') and F(ab')$_2$.

In a further embodiment, the nuclear localization sequence is as set forth in SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14.

In another embodiment, wherein the cholic acid variant is deoxycholic acid, chenodeoxycholic acid, lithocholic acid, ursodeoxycholic acid, glycocholic acid, glycochenodeoxycholic acid, or glycoursodeoxycholic acid.

In another embodiment, the antibody is trastuzumab antibody. In an embodiment, said antibody is conjugated to deruxtecan (topoisomerase inhibitor) or to DM1 (microtubule inhibitor) drug.

In a further embodiment, the conjugated compound further comprises a payload covalently linked to the antibody.

In another embodiment, the payload is an imaging molecule.

In an embodiment, the payload is fluorescence molecules, IRM imaging agent or a radionuclide.

In an embodiment, the fluorescence molecule is 4,4-difluoro-8-(4-carboxyphenyl)-1,3,5,7-tetramethyl-4-bora-3a,4a-diaza-s-indacene (BODIPY).

In another embodiment, the radionuclide is a imaging and/or therapeutic radionuclide.

In an embodiment, the radionuclide is at least one of $^{47}$Sc, $^{51}$Cr, $^{52m}$Mn, $^{55}$Co, $^{58}$Co, $^{52}$Fe, $^{56}$Ni, $^{57}$Ni, $^{61}$Cu, $^{62}$Cu, $^{64}$Cu, $^{67}$Cu, $^{66}$Ga, $^{68}$Ga, $^{67}$Ga, $^{72}$As, $^{77}$As, $^{89}$Zr, $^{90}$Y, $^{94}$mTc, $^{99}$mTc, $^{97}$Ru, $^{105}$Rh, $^{109}$Pd, $^{111}$Ag, $^{110}$In, $^{111}$In, $^{113}$mIn, $^{114}$mIn, $^{117}$mSn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi, $^{213}$Bi, $^{11}$C, $^{75}$Br, $^{76}$Br, $^{77}$Br, $^{82}$Br, $^{18}$F, $^{120}$I, $^{123}$I, $^{124}$I, $^{125}$I, $^{131}$I, $^{89}$Sr and $^{225}$Ac.

In another embodiment, the payload is a small molecule toxin.

In another embodiment, the small molecule toxin is a chemotherapeutic agent.

In another embodiment, the small molecule toxin is a microtubule disrupting agent, a DNA targeting agent as RNA polymerase inhibitor or a topoisomerase inhibitor.

In a further embodiment, the small molecule toxin is vinblastine, emtansine, Monomethyl auristatin E, or Deruxtecan.

In an additional embodiment, the conjugated compound described herein is for detecting prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

In an embodiment, the conjugated compound described herein is for treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is also provided herein of the use of the conjugated compound as described herein for treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is further provided the use of the conjugated compound as described herein in the manufacture of a medicament for treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is additionally provided herein the use of the conjugated compound as described herein for detecting prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis.

It is also provided a method of treating and/or detecting prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia, colorectal cancer, Hodgkin's lymphoma, non-Hodgkin's lymphoma, or Langerhans cell histiocytosis in a subject comprising administering to said subject the conjugated compound as described herein.

In an embodiment, the subject is a human or an animal.

It is also provided a composition comprising the conjugated compound defined herein and a payload.

In an embodiment, the composition further comprises a carrier.

BRIEF DESCRIPTION OF THE DRAWINGS

Reference will now be made to the accompanying drawings.

DETAILED DESCRIPTION

Figure 1:
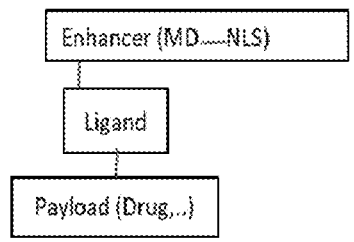
FIG. 1 illustrates a schematic representation of the conjugated compound encompassed herein wherein the antibody (ligand) is the central component on which the enhancer composed by a nuclear localisation signal (NLS) chemically linked to a sterol derivative and payload are covalently linked thereto.

It is provided a novel design of compound-conjugates specific against rapidly internalizing receptors to link endosome escape and enhanced cellular uptake. More specifically, it is provided a conjugated compound comprising an antibody covalently linked to enhancer moiety composed by a nuclear localization sequence (NLS), covalently linked to a sterol variant, such as cholic acid (ChAc) or a variant thereof. The enhancer moiety as encompassed herein is able to induce endosome escape of the compound-conjugates by direct membrane destabilization or indirectly by ROS and ceramide production which destabilize endosome-lysosome membrane.

Accordingly, it is provided a conjugated compound comprising an antibody covalently linked to a nuclear localization sequence (NLS), said NLS covalently linked to a sterol variant, excluding ChAc-SV40 large T antigen NLS (SEQ ID NO: 1).

It is known that each bile acid can have different impact on drug formulation and not result in an increase in bioavailability and delivery to specific tissues. Furthermore, the SV40 large T antigen sequence is not predictable for any other NLW sequence as it is not evident that other combination will acquire the desired intracellular and nuclear delivery activity.

In an embodiment, the conjugated compound further comprises a payload covalently linked to the antibody.

In an embodiment, the sterol variant can be positioned as provided herein on the C terminal or N terminal portion of the conjugated compound.

It is thus provided a composition comprising the conjugated compound as described herein, a payload, and a carrier.

It is provided for example a conjugated compound that escape from entrapment inside the endosome-lysosome system followed by translocation to the nucleus.

Example of conjugated compounds include, and not limited to, an antibody, an oligonucleotide, an antisense, a drug, or an siRNA molecule, and not excluded are any small molecule or biological for which it has an intracellular target, that cannot penetrate mammalian membranes.

In an embodiment, the antibody is a monoclonal or polyclonal antibody.

In an embodiment, the antibody is a monospecific, bispecific or multispecific antibody.

In another embodiment, the antibody is a mouse antibody, a goat antibody, a human antibody or a rabbit antibody, or a humanized antibody.

Also encompassed herein, the antibody might comprise an epitope binding fragment such as for example Fv, F(ab'), and/or $F(ab')_2$.

In an embodiment, it is encompassed the attachment of a sterol variant. The term "variant" in regards to a sterol variant is well known. Bile acids core is based on sterol molecule. Cholic acid is a primary bile acid which is synthesized in liver cells, which is further processed to produce secondary primary bile acids or variant of cholic acid such as for example deoxycholic acid, chenodeoxycholic acid or lithocholic acid. A cholic acid variant as encompassed herein can be deoxycholic acid, chenodeoxycholic acid, lithocholic acid, ursodeoxycholic acid, glycocholic acid, glycochenodeoxycholic acid, and/or glycoursodeoxycholic acid.

It is the conjugation of the NLS and ChAC (ChAcNLS) which allows efficient endosome escape and nuclear localization of the antibody. Bile acids trigger enzyme acid sphingomyelinase to cleave sphingomyelin which is abundantly present on the inner leaflet of endosomes. Increased amounts of ceramide destabilize membranes by forming channels or lipid flip-flop sufficient for proteins to cross, and thus the linkage of ChAc to the NLS enables the mAbs to efficiently localize in the nucleus as demonstrated in the present application by increasing potency of antibody conjugates and further explored in the enclosed. Thus the efficiency of the conjugated compound to localize to the nucleus does not depend only on the sequence of the NLS, but also on its conjugation to a biliary acid such as ChAc for inducing its escape from endosome/lysosome entrapment.

It is thus disclosed a conjugated compound comprising an antibody covalently linked to a nuclear localization sequence (NLS), said NLS covalently linked to cholic acid (ChAc) or a variant thereof, said NLS being a classical nuclear localization sequence (mono-bipartite), a hydrophobic PY-NLS or a basic PY-NLS, nucleolar localization signal, excluding ChAc-SV40NLS.

As encompassed herein, the NLS conjugated can be a classical nuclear localization sequence. Alternatively, also encompassed is a hydrophobic PY-NLS and basic PY-NLS. In an embodiment, the NLS is PQBP1 NLS (SEQ ID NO: 2), hnRNPA1 (SEQ ID NO: 3), GWG-SV40 NLS (SEQ ID NO: 4), NLS2 RPS1 (SEQ ID NO: 5), NLS1 RPS17 (SEQ ID NO: 6), NLS3 RPS17 (SEQ ID NO: 7), nucleoplasmin NLS (SEQ ID NO: 8), cMyc NLS (SEQ ID NO: 9), TUS NLS (SEQ ID NO: 10), hnRNP D NLS (SEQ ID NO: 11), hnRNP M NLS (SEQ ID NO: 12), HuR NLS (SEQ ID NO: 13), and/or NLS2-RG RPS17 (SEQ ID NO: 14).

As further encompassed, the NLS can be the SV40NLS conjugated to a sterol variant other than ChAc, such as e.g. deoxycholic acid, chenodeoxycholic acid, lithocholic acid, ursodeoxycholic acid, glycocholic acid, glycochenodeoxycholic acid, or glycoursodeoxycholic acid.

The 13-mer peptide (CGYGPKKKRKVGG; SEQ ID NO:1) that is non-cell penetrating and harbors a segment of the classical NLS (underlined) from SV-40 large T-antigen has been conjugated previously to the anti-CD123 (IL-3Rα) antibody (7G3) and its chimeric version (CSL360) (Leyton et al., 2011, J Nucl Med, 52:1465-1473). NLS-7G3 and NLS-CSL360 transporting conjugated indium-111 ($^{111}$In) were used to evaluate for their ability to route to the nucleus. Even though the presence of the NLS sequence, the proportion of radioactivity delivered in the nucleus was very low whereas the majority of the radioactivity remained on the cell surface or in the cytoplasm (Zerashkian et al., 2014, Nucl Med Biol, 41: 377-383). Thus $^{111}$In-NLSCSL360 remained trapped within the endosome.

It was disclosed in WO2017/156630, the content of which is incorporated herein in its entirety, the coupling of cholic acid which was coupled to the peptide CGYGPKKKRKVGG (SEQ ID NO:1) containing a segment of the nuclear localization sequence (NLS) from SV40 large T antigen.

As provided herewith, conjugated ("Accum") peptide variants as listed in Table 1 where synthesized following the method described in WO2017/156630. In a single tube, at least 2 mg of TDM1 for each Accum peptide variant conjugation were pooled. For example, if 10 Accum peptide variant conjugation reactions are prepared at the same time, 20 mg of TDM1 were aliquoted in a single tube. Tenfold excess of SM(PEG)4 crosslinker were added and incubated at RT for 1 h. Following first 1 h step reaction, at least 2 mg of TDM-PEG4-maleimide were aliquot in different tubes for the second step reaction, Accum peptide variant addition. Tenfold excess of selected Accum peptide variant were added in each tube reaction for 1 h at RT or O/N at 4 C. Unreacted crosslinker and Accum peptide variant were removed by G25 Sephadex and 100 kDa cut-off filter. Accum-TDM1 variant low DAR constructs were passed through 0.22 um filter to remove all potential aggregation or contamination.

TABLE 1

List of tested classical NLS and PY-NLS peptides conjugated to T-DM1 or T-Deruxtecan.

| Named | Sequence | NLS named | Type NLS |
|---|---|---|---|
| CA-C-SV40NLS | cholic acid-C-GYGPKKKRKVGG-nh2 SEQ ID NO: 1 | SV40 NLS | Classical NLS |
| C-SV40NLS-CA | C-GYGPKKKRKVGG-K(cholic acid)-NH2 | | |
| SV40NLS-C-CA | GYGPKKKRKVGG-C-K(cholic acid)-NH2 | | |
| CDCA-C-SV40NLS | chenodeoxycholic acid -C-GYGPKKKRKVGG-nh2 | | |
| DCA-C-SV40NLS | Deoxycholic acid-C-GYGPKKKRKVGG-nh2 | | |
| LCA-C-SV40NLS | Lithocholic acid-C-GYGPKKKRKVGG-nh2 | | |
| UDCA-C-SV40NLS | Ursodeoxycholic acid-C-GYGPKKKRKVGG-nh2 | | |
| GCA-C-SV40NLS | Glycocholic acid-C-GYGPKKKRKVGG-nh2 | | |
| GCDCA-C-SV40NLS | Glycochenodeoxycholic acid-C-GYGPKKKRKVGG-nh2 | | |
| GDCA-C-SV40NLS | Glycodeoxycholic acid-C-GYGPKKKRKVGG-nh2 | | |
| LCA-C-PQBP1 | Lithocholic acid-C-ADREEGKERRHHRREELAPY-NH2 | PQBP1 NLS | Hydrophobic and basic PY-NLS |
| GUDCA-C-PQBP1 | GlycoUrsodeoxycholic acid-C-ADREEGKERRHHRREELAPY-NH2 | | |
| CA-C-hnRNPA1 M9NLS | cholic acid -C-SNFGPMKGGNFGGRSSGPY-NH2 | hnRNPA1 | Hydrophobic PY-NLSs and basic PY-NLS |
| CA-C-GWG-SV40NLS | cholic acid -C-GWWGYGPKKKRKVGGWWG-NH2 | GWG-SV40 NLS | Classical NLS |
| CA-C-NLS2-RSP17 | cholic acid -C-NKRVCEEIAIIPSKKLRNK-NH2 | NLS2 RPS17 | Classical NLS |
| GCDCA-C-NLS2-RSP17 | Glycochenodeoxycholic acid-C-NKRVCEEIAIIPSKKLRNK-NH2 | | |
| LCA-C-NLS2-RSP17 | Lithocholic acid-C-NKRVCEEIAIIPSKKLRNK-NH2 | | |
| CA-C-NLS1 RPS17 (1-13) | Cholic acid-C-MGRVRTKTVKKAAGG-nh2 | NLS1 RPS17 | Classical NLS |
| CA-C-NLS3-RPS17 (43-61) | cholic acid -C-SKKLRNKIAGYVTHLMKRI-NH2 | NLS3 RPS17 | Classical NLS |
| CA-C-nucleoplasmin NLS | Cholic acid-C-AVKRPAATKKAGQAKKKKLD-nh2 | nucleoplasmin NLS | Classical NLS |
| CA-cMyc NLS | Cholic acid-C-GYGPAAKRVKLDGG-nh2 | cMyc NLS | Classical NLS |
| CA-TUS NLS | Cholic acid-C-GYGKLKIKRPVKGG-nh2 | TUS NLS | Classical NLS |

TABLE 1-continued

List of tested classical NLS and PY-NLS peptides conjugated to T-DM1 or T-Deruxtecan.

| Named | Sequence | NLS named | Type NLS |
|---|---|---|---|
| CA-C-hnRNP D NLS | Cholic acid-C-SGYGKVSRRGGHQNSYKPY-nh2 | hnRNP D NLS | Hydrophobic PY-NLSs and basic PY-NLS |
| CA-C-hnRNP M NLS | Cholic acid-C-NEKRKEKNIKRGGNRFEPY-nh2 | hnRNP M NLS | Hydrophobic PY-NLSs and basic PY-NLS |
| CA-C-HUR NLS | Cholic acid-C-GRFSPMGVDHMSGLSGVNVPG-nh2 | HuR NLS | Hydrophobic PY-NLSs and basic PY-NLS |
| CA-NLS2-RG RSP17 | Cholic acid-C-NKRVCEEIAIIPSKKLRNKGSGRIQRGPVRGIS-nh2 | NLS2-RG RPS17 | Nucleolar localization signal (classical NLS + RG domain) |

Following synthesis of the Accum construct described hereinabove, cytotoxicity assay were conducted. In Day 0, 5000 of JIMT-1 cells were plated per well in 96 well plate. In Day 1, cells were treated with TDM1 or with each Accum-TDM1 variants at concentration between 0-100 ug/ml. Cells were incubated for 72 h at 370. To determine cell viability, Prestoblue assays were used according to manufacturer protocol.

TABLE 2

Cytotoxicity of Accum-TDM1 variants at 0.1 ug/ml and 1 ug/ml

| | | TDM1- bile acid-SV40 variants | | | | | | | | |
|---|---|---|---|---|---|---|---|---|---|---|
| concentration (ug/ml) | TDM1 | TDM1-CA-SV40 | TDM1-SV40-CA | TDM1-CDCA-SV40 | TDM1-DCA-SV40 | TDM1-LCA-SV40 | TDM1-UDCA-SV40 | TDM1-GCA-SV40 | TDM1-GCDCA-SV40 | TDM1-GDCA-SV40 |
| 0.10 | 0.95 | 0.69 | 0.88 | 0.71 | 0.72 | 0.88 | 0.76 | 0.66 | 0.87 | 0.80 |
| 1.00 | 0.66 | 0.29 | 0.59 | 0.35 | 0.38 | 0.38 | 0.55 | 0.44 | 0.53 | 0.58 |

| | | TDM1- CA-NLS variants | | | | | | | |
|---|---|---|---|---|---|---|---|---|---|
| concentration (ug/ml) | TDM1 | TDM1-CA-GWG-SV40 | TDM1-CA-nucleoplasmin | TDM1-CA-cMyc | TDM1-CA-TUS | TDM1-CA-hnRNPA1 | TDM1-CA-hnRNPD | TDM1-CA-hnRNPM | TDM1-CA-Hur |
| 0.10 | 0.95 | 0.79 | 0.70 | 0.75 | 0.77 | 0.76 | 0.72 | 0.85 | 0.71 |
| 1.00 | 0.66 | 0.49 | 0.39 | 0.35 | 0.36 | 0.64 | 0.28 | 0.31 | 0.37 |

| | | TDM1- bile acid-NLS variants | | | | | | | |
|---|---|---|---|---|---|---|---|---|---|
| concentration (ug/ml) | TDM1 | TDM1-CA-NLS1 RPS17 | TDM1-CDCA-NLS1 RPS17 | TDM1-CA-NLS2 RPS17 | TDM1-LCA-NLS2 RPS17 | TDM1-CA-NLS2-RG RPS17 | TDM1-GCDCA-NLS2 RPS17 | TDM1-LCA-PQBP1 | TDM1-GUDCA-PQBP1 |
| 0.10 | 0.95 | 0.70 | 0.89 | 0.86 | 0.67 | 0.81 | 0.74 | 0.89 | 1.07 |
| 1.00 | 0.66 | 0.26 | 0.51 | 0.48 | 0.22 | 0.46 | 0.25 | 0.40 | 0.40 |

Figure 2:
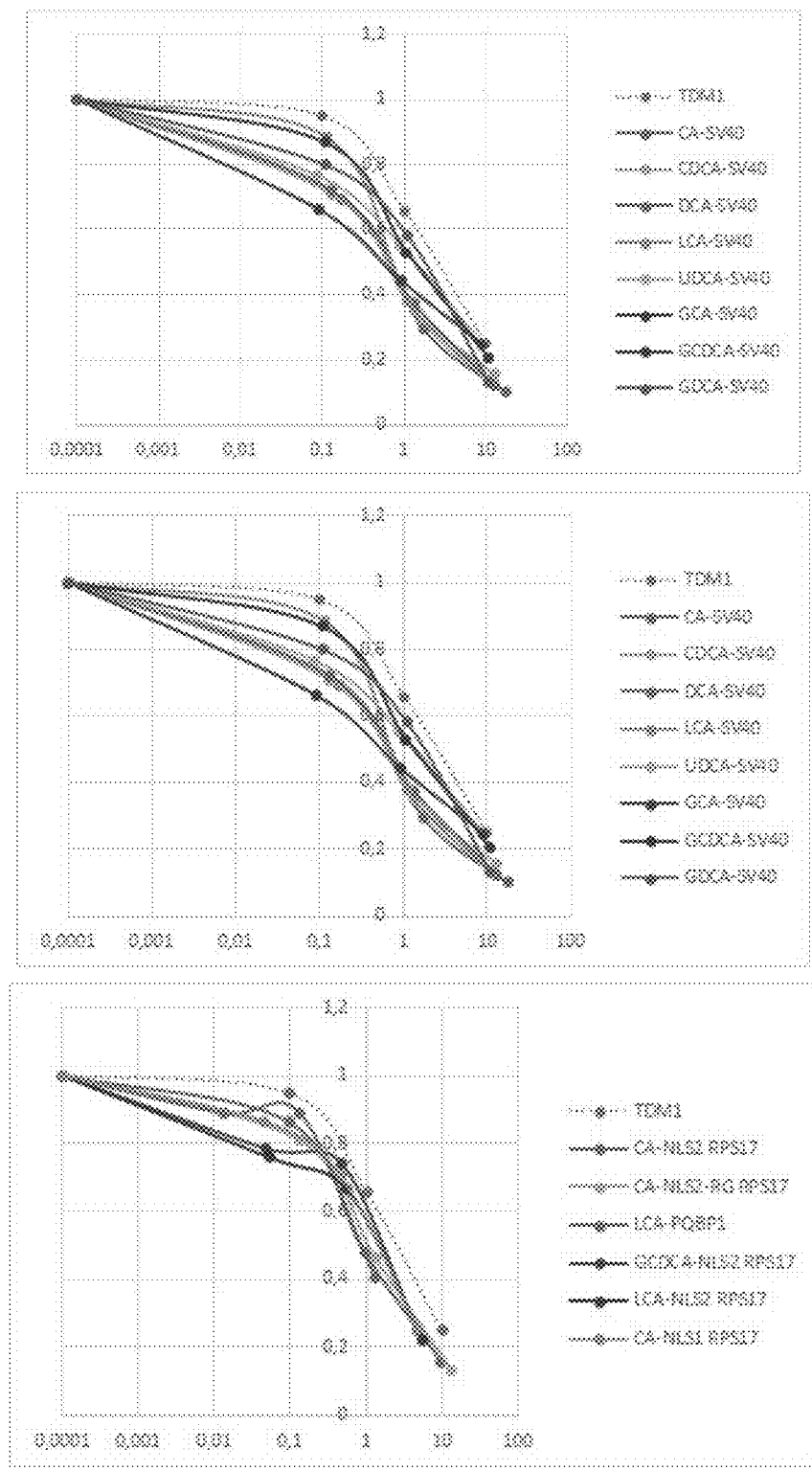
FIG. 2 illustrates graphics of cytotoxicity assay of Accum-TDM1 variants.

As seen in FIG. 2 and Table 2, each Accum variant construct increase the cytotoxicity of TDM1. At concentration of 0.1 ug/ml and 1 ug/ml of TDM1, only 5% and 34% of cell death was respectively observed but with the Accum-TDM1 constructs the cytotoxicity increase between 11-34% at 0.1 ug/ml and between 36%-88% of cell death (Table 2). In FIG. 2, it is clearly observed that a higher concentration of TDM1 is needed to induce cell death at the same efficacy than Accum-TDM1 contructs. In resume, each Accum variant low DAR constructs (1-3 Accum moiety per antibody) increase the cytotoxicity of TDM1 by a factor between 2-10.

accumulation of an antibody clearly established but the conjugated compound provided herewith does not affect the antibody's affinity and selectivity.

In general, the attachment of ChAcNLS to mAbs can be controlled.

It is also described the ability of the conjugated compound further linked to a payload such as $^{64}$Cu to enhance the cellular uptake of $^{64}$Cu. Thus ChAcNLS should not disrupt the in vivo pharmacokinetics of antibodies. The conjugated compounds provided herein can lead to more effective

TABLE 3

Cytotoxicity of Accum-T-deruxtecan variants at 0.001 ug/ml and 0.1 ug/ml

T-Deruxtecan- bile acid-NLS variants

| concentration (ug/ml) | T-Deruxtecan | T-Deruxtecan-CA-SV40 | T-Deruxtecan-CDCA-SV40 | T-Deruxtecan-GCA-SV40 | T-Deruxtecan-CA-Hur | T-Deruxtecan-CA-nucleoplasmin | T-Deruxtecan-CA-NLS1 RPS17 | T-Deruxtecan-CA-hnRNPD |
|---|---|---|---|---|---|---|---|---|
| 0.001 | 0.87 | 0.73 | 0.83 | 0.73 | 0.79 | 0.79 | 0.84 | 0.63 |
| 0.1 | 0.54 | 0.47 | 0.51 | 0.49 | 0.43 | 0.46 | 0.55 | 0.43 |

Figure 3:
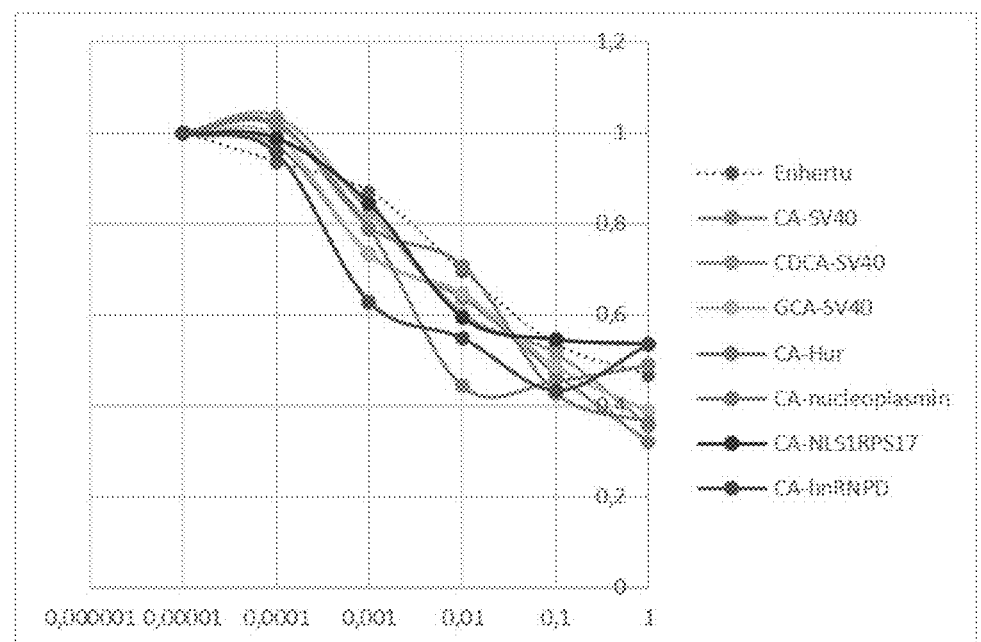
FIG. 3 illustrates graphics of cytotoxicity assay of Accum-T-deruxtecan variants.

As seen in FIG. 3 and Table 3, each Accum variant construct increase the cytotoxicity of T-deruxtecan. At concentration of 0.001 ug/ml and ug/ml of 0.1 T-deruxtecan, only 87% and 54% of cell death was respectively observed but with the Accum-T-deruxtecan constructs the cytotoxicity increase between 63-84% and between 43-51% of cell death respectively (Table 3). In FIG. 3, it is clearly observed that a higher concentration of T-deruxtecan is needed to induce cell death at the same efficacy than Accum-T-deruxtecan constructs. In resume, each Accum variant low DAR constructs (1-3 Accum moiety per antibody) increase the cytotoxicity of T-deruxtecan by a factor between 2-10.

Accordingly, it is provided an antibody, such as for example the Trastuzamab in a breast cancer system, but not limited to, or a small molecule conjugated as described herein.

Also encompassed herein, but not limited, the payload encompassed herein is a radionuclide conjugated to the compound described herein which is selected from $^{47}$Sc, $^{51}$Cr, $^{52m}$Mn, $^{55}$Co, $^{58}$Co, $^{52}$Fe, $^{56}$Ni, $^{57}$Ni, $^{61}$Cu, $^{62}$Cu, $^{64}$Cu, $^{67}$Cu, $^{66}$Ga, $^{68}$Ga, $^{67}$Ga, $^{72}$As, $^{77}$As, $^{89}$Zr, $^{90}$Y, $^{94m}$Tc, $^{99m}$Tc, $^{97}$Ru, $^{105}$Rh, $^{109}$Pd, $^{111}$Ag, $^{10}$In, $^{111}$n, $^{113}$min, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi, $^{213}$Bi, $^{11}$C, $^{75}$Br, $^{76}$Br, $^{77}$Br, $^{82}$Br, $^{18}$F, $^{120}$I, $^{123}$I, $^{124}$I, $^{125}$I, $^{131}$I, $^{89}$Sr and $^{225}$Ac. In addition, also encompassed are a chemotherapeutic conjugated as described herein, as for example DM1 (mertansine) and Deruxtecan but not limiting.

Accordingly, it is provided in an embodiment, a novel cholic acid (ChAc)-NLS fusion peptide (ChAcNLS) conjugated to an antibody as depicted in FIG. 1, which functionalizes this complex to escape endosome entrapment and route to and utilize the nucleus as a reservoir to enhance intracellular accumulation. When ChAcNLS is conjugated to a mAb and the complex radiolabeled with copper-64 ($^{64}$Cu) and injected in vivo, the amount of radioactivity delivered to a tumor for example is superior to versions that cannot escape endosome entrapment. Not only is the conjugated compound ability to change enhance intracellular accumulation of an antibody clearly established but the conjugated compound provided herewith does not affect the antibody's affinity and selectivity.

radiotoxicity or higher sensitive detection of cancer cells because of the observed increases in radioactive retention as shown herein in tumors.

It is thus provided a way to widely adapt other molecule or antibody by targeting rapidly internalizing receptors. Many interleukin receptors implicated in a variety of cancers undergo rapid endocytosis upon ligand binding. The use of a conjugate as described herein can increase accumulation of actual chemotherapeutic molecule for example in targeted cells.

In an embodiment, the antibody-drug conjugates (ADCs) as described herein are composed of three components—a monoclonal antibody (mAb), cross-linker, and a cytotoxin (e.g. small molecule chemotherapeutic). For example, the cytotoxin is conjugated to the mAb via the cross-linker.

It is encompassed herein that the antibody-drug conjugates (ADCs) as described herein comprises a payload such as a small molecule toxin such as for example and not limited to, microtubule disrupting agents (such as vinblastine, Monomethyl auristatin E or MMAE, DM1) and/or DNA targeting agents (Deruxtecan, Topoisomerase inhibitor).

For example, an antibody conjugated with ChAcNLS together with an attached chemotherapeutic molecule such as 4,4-difluoro-8-(4-carboxyphenyl)-1,3,5,7-tetramethyl-4-bora-3a,4a-diaza-s-indacene (BODIPY for short), which is a cytotoxic molecule used in photodynamic therapy applications in cancer, results in an increase cytoplasmic accumulation of the antibody and chemotherapeutic molecule since ChAcNLS does not interfere with tumor targeting, provides faster blood clearance and at the same time better tumor uptake.

Not only the conjugate as described herein provides a mean to enhance delivery of an antibody, but ChAcNLS can enhance the delivery of an attached molecular payload, not just the antibody. ChAcNLS can deliver increased amounts of a molecular payload to the nucleus.

It is further encompassed herein the possibility of not only conjugate an antibody as described herein but also conjugating the antibody with a further drug, such as vinblastine, which is used in combination with other chemotherapy drugs to treat Hodgkin's lymphoma (Hodgkin's disease) and non-Hodgkin's lymphoma, and cancer of the testicles. It is also used to treat Langerhans cell histiocytosis.

Accordingly, the conjugated compound described herein can be used for detecting or treating prostate cancer, breast cancer, liver cancer, stomach cancer, colon cancer, pancreatic cancer, ovarian cancer, lung cancer, kidney cancer, brain cancer, testicular cancer, glioblastoma, sarcoma, bone cancer, head-and-neck cancers, skin cancer, lymphomas, leukemia or colorectal cancer.

While the present disclosure has been described in connection with specific embodiments thereof, it will be understood that it is capable of further modifications and this application is intended to cover any variations, uses, or adaptations of the including such departures from the present disclosure as come within known or customary practice within the art to which the invention pertains and as may be applied to the essential features hereinbefore set forth, and as follows in the scope of the appended claims.

What is claimed is:

1. A conjugated compound comprising an antibody or an epitope-binding fragment thereof, covalently linked to a peptide comprising a nuclear localization sequence (NLS) of SEQ ID NO:6, said peptide covalently linked to a bile acid, wherein the conjugated compound further comprises a payload for intracellular accumulation covalently linked to the antibody or epitope-binding fragment thereof.

2. The conjugated compound of claim 1, wherein the bile acid comprises or consists of: cholic acid (CA), deoxycholic acid (DCA), chenodeoxycholic acid (CDCA), lithocholic acid (LCA), ursodeoxycholic acid (UDCA), glycocholic acid (GCA), glycochenodeoxycholic acid (GCDCA), glycodeoxycholic acid (GDCA), or glycoursodeoxycholic acid (GUDCA).

3. The conjugated compound of claim 1, wherein the bile acid comprises or consists of a variant of CA, DCA, CDCA, LCA, UDCA, GCA, GCDCA, GDCA, or GUDCA, wherein the variant triggers ceramide accumulation on the inner leaflet of endosomes and/or triggers increased acid sphingomyelinase (ASM)-mediated cleavage of sphingomyelin to form ceramide.

4. The conjugated compound of claim 1, wherein the bile acid comprises or consists of a primary bile acid.

5. The conjugated compound of claim 1, wherein the bile acid comprises or consists of a secondary bile acid.

6. The conjugated compound of claim 1, wherein the epitope-binding fragment comprises or consists of: Fv, F(ab'), or F(ab')2.

7. The conjugated compound of claim 1, wherein the payload comprises or consists of a radionuclide.

8. The conjugated compound of claim 7, wherein the radionuclide is at least one of $^{47}$Sc, $^{51}$Cr, $^{52m}$Mn, $^{55}$Co, $^{58}$Co, $^{52}$Fe, $^{56}$Ni, $^{57}$Ni, $^{61}$Cu, $^{62}$Cu, $^{64}$Cu, $^{67}$Cu, $^{66}$Ga, $^{68}$Ga, $^{67}$Ga, $^{72}$As, $^{77}$As, $^{89}$Zr, $^{90}$Y, $^{94m}$Tc, $^{99m}$Tc, $^{97}$Ru, $^{105}$Rh, $^{109}$Pd, $^{111}$Ag, $^{110}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{201}$Tl, $^{203}$Pb, $^{211}$At, $^{212}$Bi, $^{213}$Bi, $^{11}$C, $^{75}$Br, $^{76}$Br, $^{77}$Br, $^{82}$Br, $^{18}$F, $^{120}$I, $^{123}$I, $^{124}$I, $^{125}$I, $^{131}$I, $^{89}$Sr, and $^{225}$Ac.

9. The conjugated compound of claim 1, wherein the payload comprises or consists of a small molecule toxin.

10. The conjugated compound of claim 1, wherein the payload comprises or consists of a chemotherapeutic agent.

11. The conjugated compound of claim 10, wherein the chemotherapeutic agent comprises or consists of a microtubule disrupting agent, a DNA targeting agent, an RNA polymerase inhibitor, a topoisomerase inhibitor, or a DNA alkylated agent.

12. The conjugated compound of claim 1, wherein the payload comprises or consists of an imaging molecule.

13. The conjugated compound of claim 12, wherein the imaging molecule comprises a fluorescence molecule or a radionuclide.

14. A method for treating or detecting cancer in a subject, the method comprising:
    (a) providing the conjugated compound of claim 1, wherein the antibody or epitope-binding fragment thereof specifically binds to an epitope expressed on the subject's cancer cells, and wherein the payload comprises or consists of a chemotherapeutic agent or an imaging agent; and
    (b) administering the conjugated compound to the subject.

* * * * *

```
                        SEQUENCE LISTING

Sequence total quantity: 14
SEQ ID NO: 1            moltype = AA  length = 13
FEATURE                 Location/Qualifiers
REGION                  1..13
                        note = Synthesized petpide
source                  1..13
                        mol_type = protein
                        organism = synthetic construct
SEQUENCE: 1
CGYGPKKKRK VGG                                                              13

SEQ ID NO: 2            moltype = AA  length = 20
FEATURE                 Location/Qualifiers
REGION                  1..20
                        note = Synthesized petpide
source                  1..20
                        mol_type = protein
                        organism = synthetic construct
SEQUENCE: 2
ADREEGKERR HHRREELAPY                                                       20

SEQ ID NO: 3            moltype = AA  length = 19
FEATURE                 Location/Qualifiers
REGION                  1..19
                        note = Synthesized petpide
source                  1..19
                        mol_type = protein
                        organism = synthetic construct
SEQUENCE: 3
SNFGPMKGGN FGGRSSGPY                                                        19

SEQ ID NO: 4            moltype = AA  length = 18
FEATURE                 Location/Qualifiers
REGION                  1..18
                        note = Synthesized petpide
source                  1..18
                        mol_type = protein
                        organism = synthetic construct
SEQUENCE: 4
GWWGYGPKKK RKVGGWWG                                                         18

SEQ ID NO: 5            moltype = AA  length = 19
FEATURE                 Location/Qualifiers
REGION                  1..19
                        note = Synthesized petpide
source                  1..19
                        mol_type = protein
                        organism = synthetic construct
SEQUENCE: 5
NKRVCEEIAI IPSKKLRNK                                                        19

SEQ ID NO: 6            moltype = AA  length = 15
FEATURE                 Location/Qualifiers
REGION                  1..15
                        note = Synthesized petpide
source                  1..15
                        mol_type = protein
                        organism = synthetic construct
SEQUENCE: 6
MGRVRTKTVK KAAGG                                                            15

SEQ ID NO: 7            moltype = AA  length = 19
FEATURE                 Location/Qualifiers
REGION                  1..19
                        note = Synthesized petpide
source                  1..19
```

```
                              mol_type = protein
                              organism = synthetic construct
SEQUENCE: 7
SKKLRNKIAG YVTHLMKRI                                                        19

SEQ ID NO: 8                  moltype = AA   length = 20
FEATURE                       Location/Qualifiers
REGION                        1..20
                              note = Synthesized petpide
source                        1..20
                              mol_type = protein
                              organism = synthetic construct
SEQUENCE: 8
AVKRPAATKK AGQAKKKKLD                                                       20

SEQ ID NO: 9                  moltype = AA   length = 14
FEATURE                       Location/Qualifiers
REGION                        1..14
                              note = Synthesized petpide
source                        1..14
                              mol_type = protein
                              organism = synthetic construct
SEQUENCE: 9
GYGPAAKRVK LDGG                                                             14

SEQ ID NO: 10                 moltype = AA   length = 14
FEATURE                       Location/Qualifiers
REGION                        1..14
                              note = Synthesized petpide
source                        1..14
                              mol_type = protein
                              organism = synthetic construct
SEQUENCE: 10
GYGKLKIKRP VKGG                                                             14

SEQ ID NO: 11                 moltype = AA   length = 19
FEATURE                       Location/Qualifiers
REGION                        1..19
                              note = Synthesized petpide
source                        1..19
                              mol_type = protein
                              organism = synthetic construct
SEQUENCE: 11
SGYGKVSRRG GHQNSYKPY                                                        19

SEQ ID NO: 12                 moltype = AA   length = 19
FEATURE                       Location/Qualifiers
REGION                        1..19
                              note = Synthesized petpide
source                        1..19
                              mol_type = protein
                              organism = synthetic construct
SEQUENCE: 12
NEKRKEKNIK RGGNRFEPY                                                        19

SEQ ID NO: 13                 moltype = AA   length = 21
FEATURE                       Location/Qualifiers
REGION                        1..21
                              note = Synthesized petpide
source                        1..21
                              mol_type = protein
                              organism = synthetic construct
SEQUENCE: 13
GRFSPMGVDH MSGLSGVNVP G                                                     21

SEQ ID NO: 14                 moltype = AA   length = 33
FEATURE                       Location/Qualifiers
REGION                        1..33
                              note = Synthesized petpide
source                        1..33
                              mol_type = protein
                              organism = synthetic construct
SEQUENCE: 14
NKRVCEEIAI IPSKKLRNKG SGRIQRGPVR GIS                                        33
```